(12) United States Patent
Smith et al.

(10) Patent No.: US 11,446,451 B2
(45) Date of Patent: Sep. 20, 2022

(54) INHALER

(71) Applicant: 1NHALER LIMITED, Scottish Borders (GB)

(72) Inventors: Donald Smith, Edinburgh (GB); Gregor John McLennan Anderson, London (GB); Lisa Charleston Mcmyn, West Linton (GB); Alan Miller Suttie, Glasgow (GB)

(73) Assignee: INHALER LIMITED, Scottish Borders (GB)

( * ) Notice: Subject to any disclaimer, the term of this patent is extended or adjusted under 35 U.S.C. 154(b) by 193 days.

(21) Appl. No.: 16/627,726

(22) PCT Filed: Jul. 2, 2018

(86) PCT No.: PCT/GB2018/051857
§ 371 (c)(1),
(2) Date: Dec. 30, 2019

(87) PCT Pub. No.: WO2019/008336
PCT Pub. Date: Jan. 10, 2019

(65) Prior Publication Data
US 2020/0297946 A1   Sep. 24, 2020

(30) Foreign Application Priority Data
Jul. 3, 2017   (GB) ..................... 1710653

(51) Int. Cl.
*A61M 15/00*   (2006.01)

(52) U.S. Cl.
CPC ...... *A61M 15/0043* (2014.02); *A61M 15/002* (2014.02); *A61M 15/0061* (2014.02); *A61M 2202/064* (2013.01)

(58) Field of Classification Search
CPC .... A61M 15/00–0001; A61M 15/0028; A61M 15/0043; A61M 15/0061;
(Continued)

(56) References Cited

U.S. PATENT DOCUMENTS

| 1,876,591 A | 9/1932 | Bawden |
| 2,598,823 A | 6/1952 | O'Grady |

(Continued)

FOREIGN PATENT DOCUMENTS

| CN | 1437551 A | 8/2003 |
| CN | 1446111 A | 10/2003 |

(Continued)

OTHER PUBLICATIONS

International Search Report on patent application No. PCT/GB2018/051857 dated Aug. 31, 2018.

*Primary Examiner* — Rachel T Sippel
(74) *Attorney, Agent, or Firm* — Moser Taboada

(57) ABSTRACT

A device for inhaling an active agent is provided that can be moved from a first configuration to a second configuration. The device comprises two flexible substrates and a membrane located between the two flexible substrates, and the two flexible substrates being connected at two opposing edges and unconnected at two further opposing edges. An active agent provided on the membrane may be inhaled by a user when the device is in the second configuration. A method of using the device is also provided.

20 Claims, 13 Drawing Sheets

(58) Field of Classification Search
CPC ........... A61M 15/0086–0088; A61M 15/0091; A61M 2202/064
See application file for complete search history.

(56) References Cited

U.S. PATENT DOCUMENTS

| | | | |
|---|---|---|---|
| 4,058,425 | A | 11/1977 | Thrun |
| 4,508,116 | A | 4/1985 | Duncan et al. |
| 5,038,431 | A | 8/1991 | Burgin et al. |
| 6,098,619 | A | 8/2000 | Britto et al. |
| 6,105,574 | A | 8/2000 | Jahnsson |
| 6,401,710 | B1 | 6/2002 | Scheuch et al. |
| 6,550,473 | B1* | 4/2003 | Sladek ............... A61M 15/0086 128/200.22 |
| 8,413,651 | B2 | 4/2013 | Powell et al. |
| 8,807,132 | B2 | 8/2014 | Jauernig et al. |
| 10,857,315 | B2* | 12/2020 | Brown ................. B05B 11/062 |
| 2010/0163045 | A1 | 7/2010 | Powell et al. |
| 2011/0132359 | A1* | 6/2011 | Poree ................ A61M 15/0018 128/203.21 |
| 2013/0032145 | A1 | 2/2013 | Adler et al. |
| 2016/0144140 | A1 | 5/2016 | Aberg et al. |
| 2019/0151578 | A1 | 5/2019 | Dennis |

FOREIGN PATENT DOCUMENTS

| | | |
|---|---|---|
| CN | 101856154 A | 10/2010 |
| CN | 106535968 A | 3/2017 |
| EP | 1962934 A1 | 9/2008 |
| EP | 2614849 A1 | 7/2013 |
| GB | 443160 A | 2/1936 |
| GB | 2137886 A | 10/1984 |
| WO | WO-2007096023 A1 | 8/2007 |
| WO | WO-2008124666 A2 | 10/2008 |
| WO | WO-2014175815 A1 | 10/2014 |
| WO | WO-2017205907 A1 | 12/2017 |

* cited by examiner

INHALER

FIELD OF THE INVENTION

The invention relates to devices for delivery of active agents to a subject, more specifically to devices for delivery of active agents into the lungs of a subject, such as inhaler devices.

BACKGROUND

There are a number of active agents that are useful in treating various diseases or conditions that need to be administered to the subject via the lungs, i.e. they are pulmonary delivered active agents. Such pulmonary delivered active agents typically use devices that allow the subject to inhale the active agent directly into the lungs, such as inhalers.

Typically, inhalers in the art are designed to be used multiple times to minimise waste and to provide the subject with a single delivery system that they can carry with them to provide a reliable delivery system for when the subject needs them. For example, it is important for subjects suffering from asthma to have a delivery system to hand whenever they may suffer from an asthma attack for delivering the necessary active agent quickly and efficiently.

However, such inhaler devices have suffered from the active agent and the carrier used to allow the active agent to be successfully delivered to the lungs of the subject clogging up the system over time, thereby increasing the chances of the inhaler devices failing when the subject needs them. Accordingly, multiple solutions have been provided that seek to either prevent the inhaler devices becoming clogged up over time, or to ensure that when the active agent and carrier are to be delivered to the lungs of a subject they are dispersed into small particles that will not result in obstruction of the channels of the inhaler devices.

Solutions to these problems involve increasingly complicated devices that become increasingly bulky and less convenient for the subject to carry and use.

Therefore, there is a need for improved inhaler devices that are convenient to carry for a subject and that are reliable.

As a result it is at least one object of the invention to provide an improved device for delivery of active agents to the lungs of a subject.

SUMMARY

According to a first aspect of the invention there is provided a device comprising two flexible substrates and a membrane located between the two flexible substrates, the two flexible substrates being connected at two opposing edges and unconnected at two further opposing edges, wherein the device is configured to move between a first configuration where the two flexible substrates are substantially flat and in contact with one another, and a second configuration where the two flexible substrates are flexed such that a channel is formed between the two flexible substrates, wherein the membrane is configured to span the channel between the two flexible substrates when the device is in the second configuration, such that an active agent provided on the membrane may be inhaled by a user when the device is in the second configuration.

The inventor has surprisingly found that the device of the present aspect provides a simple way of delivering an active agent to the lungs of a subject, which is compact, mobile and easy to use.

Typically, the two flexible substrates are the same shape. In some embodiments the two flexible substrates may be rectangular. In some embodiments the two flexible substrates may be square. Alternatively, in other embodiments the two flexible substrates may be oblong. It will be appreciated by the person skilled in the art that alternative shapes of the two flexible substrates are included within the scope of the present disclosure, as long as the two flexible substrates are connected at two opposing edges and can move between the first configuration and the second configuration. For example, the two flexible substrates may be trapezoidal, hexagonal, octagonal or similar. In another example, the two opposed edges that are not connected may be curved.

Typically, the two flexible substrates are uniform or substantially uniform substrates that may be flexed to move from the first configuration to the second configuration. However, at least one of the two flexible substrates may comprise two or more regions that have differing rigidity such that at least one of the two or more regions is more rigid and resistant to flexing, and at least one of the two or more regions is less rigid and less resistant to flexing. For example, one or both of the flexible substrates may comprise one or more flexible portions and one or more rigid portions. The one or more rigid portions may resist flexing and the one or more flexible portions may be readily flexed. As a result during use the one or more flexible region of at least one of the two flexible substrates may flex to allow the device to move from the first configuration to the second configuration, and the one or more rigid region remains substantially planar. The flexible region may form a hinge in the flexible substrate. The flexible region may be shaped such that the device is biased towards the second configuration.

The flexible substrates may comprise card or cardboard. The flexible substrates may comprise plastic. The flexible substrates may comprise a combination of card and plastic, such as a card or cardboard substrate with a plastic coating. The plastic coating may be provided on the external surface of the flexible substrates. The plastic coating may be provided on the internal surface of the flexible substrates. The plastic coating may be provided on both the internal surface and the external surface of the flexible substrates.

One or both of the two flexible substrates may be degradable. One or both of the two flexible substrates may be biodegradable. For example, the device may degrade when contacted to water, or in the presence of bacteria or similar.

The membrane and an active agent thereon may be protected from moisture, light oxygen and contamination. The membrane may be retained within a protective pocket between the two flexible substrates. The protective pocket may open, exposing the membrane and active agent thereon when the device is moved from the first configuration to the second configuration. The protective pocket may comprise a material that is resistant to water, oxygen and/or light. For example, the protective pocket may comprise a metallic foil, such as aluminium, or a plastic film.

At least a portion of at least one side of one or both of the two flexible substrates may comprise a metallic coating. For example, at least a portion of the interior surfaces of the two flexible substrates may comprise a metallic coating. The metallic coating may be a foil coating or similar. The metallic coating may comprise aluminium, copper or tin, for example.

In some embodiments, the metallic coating covers substantially the entire interior surface of both of the two flexible substrates. In some embodiments, the metallic coating covers a portion of the interior surface of both of the two flexible substrates. The portion may be adjacent to one of the unconnected opposing ends of both of the two flexible substrates. The portion may be part way between the two opposing unconnected ends of both of the two flexible substrates.

Typically, the metallic coating is located such that the membrane is at least partially covered by the metallic coating when the device is in the first configuration and the two flexible substrates are substantially flat. In some embodiments where the two flexible substrates comprise a metallic coating, the membrane is contained within an envelope or similar where the envelope comprises the metallic coating of the two flexible substrates. The envelope may be sealed such that the membrane is sealed within the envelope. Accordingly, the active agent provided on the membrane may be protected from moisture, oxygen, light and contamination.

The envelope may be sealed adjacent to the membrane. In embodiments where substantially the entire interior surface of both of the two flexible substrates is covered by the metallic coating, the envelope formed by the metallic coatings may be sealed adjacent to one or both of the unconnected opposing ends of the two flexible substrates.

The device may be a single use device. That is, the membrane between the two flexible substrates may comprise a single dose of active agent, and once the device has been used by a subject, the device may be discarded, and replaced by a new device.

In embodiments where the two flexible substrates are degradable, the discarded devices may degrade when contacted with water etc., thereby leaving minimal waste. In embodiments where the device comprises card or plastic, the device may be recycled to minimise waste.

Typically, an active agent is located on the membrane. The active agent may be on the surface of the membrane. For example, the active agent may be in particulate form and the particles may be attached to the surface of the membrane. The active agent may be loosely attached to the surface of the membrane such that when air passes through the membrane during use, the active agent is dislodged from the membrane and becomes airborne. As a result, the active agent may be readily inhaled by a subject into their lungs.

In some embodiments, the membrane may comprise particles and the particles may comprise one or more active agents. The particles may also comprise a carrier, vehicle or excipient. The carrier, vehicle or excipient may help prevent the particles from aggregating whilst the device is in the first configuration before use. The carrier, vehicle or excipient may enhance the ability of the or each active agent to become airborne when air passes through the channel of the device when the subject inhales, for example. The carrier, vehicle or excipient may prevent the particles from aggregating on the membrane.

Typically, the active agent on the membrane is sufficient for a user to receive one full dose of the active agent when they inhale through the device. Accordingly, the amount of active agent on the membrane may correspond to a single full dose. In some embodiments, when a user inhales through the device, some active agent may remain on the membrane. Therefore, the amount of active agent on the membrane may correspond to more than a single full dose, such that the amount of active agent that is actually inhaled by the user is full dose.

Preferably, the membrane is gas permeable to allow air to pass through the membrane during use.

The membrane may be substantially continuous and provide a substantially continuous surface upon which an active agent may be mounted. For example, the membrane may have pores that allow air to pass across the membrane but that are small enough to prevent particles of active agent to pass through.

The membrane may be a mesh. The mesh may comprise a network of fibres. The network of fibres may be woven together to form the mesh. The network of fibres may be connected at nodes to form the mesh. Particles of active agent may be adhered to the surface of the fibres of the mesh.

The membrane may comprise a polymer. For example, the membrane may comprise polytetrafluoroethylene (PTFE), expanded PTFE (ePTFE), polypropylene, polyethylene, polyurethane, poly-lactic acid, poly-glycolic acid, polycaprolactone, poly(dioxanone), or a co-polymer thereof.

In embodiments where the membrane is substantially continuous, the membrane may span only portions of the cross-section of the channel to ensure that a sufficient air flow may be created through the channel during use. Accordingly, there may be gaps in the cross-section of the channel that allow an increased air flow through the channel.

The membrane may be planar, or substantially planar. Alternatively, the membrane may comprise an indented portion. In embodiments where the membrane comprises an indented portion, a majority of the active agent on the membrane may be located within the indented portion. Accordingly, the indented portion may extend away from the outlet of the device, and towards the inlet of the device. In some embodiments, during use, the indented portion pay be everted when a user breathes in through the device. Accordingly, active agent retained within the indented portion may be propelled in the direction of airflow. The membrane may span and occlude the entire cross-section of the channel when the device is in the second configuration. Typically, the membrane spans the channel between the opposed open edges of the flexible substrates. The membrane may span or occlude a portion of the channel when the device is in the second configuration. As a result there may be portions of the channel where air can pass through the channel without passing through the membrane, and portions of the channel where air must pass through the membrane.

Typically, the membrane is flexible and is folded or collapsed when the device is in the first configuration.

The membrane may be mounted within the channel on a support. The support may comprise a gas impermeable material that occludes the channel and at least one aperture.

The membrane may be mounted within the at least one aperture. Accordingly, the air flow through the channel may be constricted by the aperture within the support to thereby increase the rate of air flow through the membrane (namely, a venturi tube), thereby increasing the force exerted by the air flow on the active agent on the membrane to lift the active agent from the membrane and into the air flow.

In some embodiments, the support may comprise at least two apertures and a membrane may be supported across each aperture. Accordingly, a first membrane may be supported within a first aperture, and a second membrane may be supported within a second aperture. The first membrane may be provided with a first active agent. The second membrane may be provided with a second active agent. Therefore, the device may be configured to deliver two active agents at the same time to a user when the user inhales through the device. The first active agent may be provided in a first unit dose. The second active agent may be provided in a second unit dose. The first unit dose may be different to the second unit dose. The first unit dose may be the same as the second unit dose.

The support may occlude the channel when the device is in the first configuration. The support may adopt a flexed or folded or otherwise reversibly collapsed configuration when the device is in the first configuration. When the device is moved to the second configuration, the support may open out to span and occlude the channel of the device.

Typically, the support may open out to an open configuration and the support may not open any further. Accordingly, the support may ensure that the device may not be moved beyond the second configuration by a user, thereby ensuring that the optimum air flow is achieved by the device when the user inhales through the device in the second configuration.

Typically, the membrane is configured to ensure that during use when a subject inhales at one of the openings of the channel the air flow through the device is sufficient to dislodge a sufficient amount of the active agent or particles comprising the active agent from the membrane into the lungs of the subject to provide the dose of active agent required.

Preferably, the active agent is effective when delivered to the lungs of the subject. Therefore, the device of the present aspect is suitable for use for delivery of any active agent that may be delivered to the lungs of a subject.

Typically, the active agent is provided as a dry powder. The dry powder may comprise particles. The particles may comprise the active agent. The particles may comprise a carrier.

The active agent may be a bronchodilator. For example, the active agent may be salbutamol, salmeterol, formoterol, Ventolin, or other such.

The active agent may be a vaccine. For example, the active agent may be an inhalable vaccine against diseases such as cholera, diphtheria, anthrax, tetanus, hepatitis A or B, influenza, measles, meningitis, polio, rabies, pneumonia, rotavirus, smallpox, typhoid, yellow fever etc.

The active agent may treat pain. For example, the active agent may be an inhalable form of tramadol, gabapentin, Vicodin (registered trade mark), ibuprofen, acetaminophen, hydrocodone, naproxen, methadone, codeine, hydroxyzine, paracetamol, aspirin, etc.

The active agent may be used to treat diabetes. For example, the active agent may be an inhalable form of insulin, canagliflozin, alogliptin benzoate, dapagliflozin, empagliflozin, ranibizumab, duglaglutide, pioglitazone hydrochloride and glimepiride etc.

The active agent may be used to treat or prevent migraine. The active agent may be a triptan (or 5HT agonists) such as Almotriptan (such as Almogran™), Eletriptan (such as Relpax™), Frovatriptan (such as Migard™), Naratritan (such as Naramig™), Rizatriptan (such as Maxalt™), Sumatriptan (such as Imigran™), Zolmitriptan (such as Zomig™), or similar.

The active agent may be a hormone, such as an inhalable form of oxytocin or similar. The active agent may prevent postpartum haemorrhage.

The active agent may be used to treat sexual health disorders. For example, the active agent may be an inhalable form of sildenafil.

The active agent may also be a vitamin, a dietary supplement, a probiotic, or a natural stimulant such as caffeine, or a natural relaxant such as chamomile extract, or a herbal remedy. The active agent may be any other non-medical, inhalable agent that can be manufactured as an inhalable dry powder.

A first opening of the channel may be an air inlet and the second opening of the channel may be an air outlet such that during use air is taken into the channel via the air inlet and inhaled out of the channel via the air outlet. The active agent may be provided on one side of the membrane. The active agent may be provided on the side of the membrane facing the air outlet. For example, in embodiments where the membrane provides a substantially continuous surface, the active agent may be provided on the side of the membrane facing the air outlet.

The device may be protected from moisture. The device may be stored in waterproof packaging before use. The device may comprise one or more seals. The device may comprise one or more seals such that the membrane is sealed within the device and is thereby protected from moisture. For example, the device may comprise a seal adjacent to each opening. In another example, the device may comprise a seal either side of the membrane. During use, the action of moving the device from the first position to the second position may break the or each seal such that the membrane and any active agent mounted thereon is exposed.

In embodiments where the two flexible substrates comprise a metallic coating, the device may comprise seals at each opening of the channel and seals at either side of the metallic coating.

The device may comprise one or more reinforcing elements. The or each reinforcing element may bias the device toward the second configuration. The or each reinforcing element may provide a biasing force that is insufficient to move the device from the first configuration to the second configuration, and complements the force applied by a user to open or move the device from the first configuration to the second configuration.

The device may comprise one or more reinforcing elements in a central region of the device. The device may comprise one or more reinforcing elements adjacent to one or more of the openings of the channel. The reinforcing elements may allow the device to more readily move from the first configuration to the second configuration when a threshold pressure is applied by the user to the two opposing connected edges.

The or each reinforcing element may extend across one or both flexible substrates. The or each reinforcing element may extend across the width of the channel. That is, the or each reinforcing element may extend between the connected edges of the or each flexible substrate.

The or each reinforcing element may be shaped to promote opening of the channel when the two flexible substrates are flexed. For example, the or each reinforcing element may be curved or bent such that when pressure is applied to the connected opposing edges, the device is biased toward the second configuration.

The device may be dimensioned to fit within a user's hand. In some embodiments the device may be dimensioned to fit within a user's wallet or purse. For example, the device may be the size of a typical credit card or similar (i.e. generally planar having two major dimensions approximately 86 mm by 54 mm). As a result, the device may be retained by a user in their wallet or purse to ensure that the device is readily to hand should the user require a dose of the active agent.

In some embodiments, the channel is configured to optimise air flow through the channel.

The cross-section of the channel may decrease from the air inlet to the air outlet, such that the air flow through the channel is accelerated from the air inlet to the air outlet.

The cross-section of the channel may be reduced in a portion of the channel. The cross-section of the channel may be reduced in a portion of the channel between the air inlet and the air outlet.

The channel may comprise a first portion and a second portion. The cross-section of the channel within the first portion may be larger than the cross section of the second portion. Accordingly, where the rate of air flow is constant through the channel, the air must travel more quickly through the second portion compared to the first portion.

The second portion may comprise an aperture that constricts the channel. The membrane may span the aperture such that air flowing through the second portion must flow through the membrane. Accordingly, the air is moving faster through the membrane than through the first portion of the channel, thereby imposing a greater force on the active agent present on the membrane to lift that active agent into the air flow.

In some embodiments the channel may extend across the full width of the two flexible substrates. In alternative embodiments, the channel may extend across only a portion of the full width of the two flexible substrates. The two flexible substrates may comprise features such as creases or more pliant portions that define the width of the channel. For example, the two flexible substrates may comprise creases that run along the length of the two flexible substrates and that are spaced from the opposed connected edges of the two flexible substrates. During use, when the user moves the device from the first configuration to the second configuration, the channel is formed between the two creases, and the two flexible substrates remain substantially flat between the crease and associated connected edge either side of the channel.

The device may comprise an element that restricts the maximum extent to which the two flexible substrates can be flexed to move the device to the second configuration. For example, the device may comprise one or more connectors attached to each of the two flexible substrates such that when the device is in the second configuration, the separation of the two flexible substrates is determined by the length of the or each connector. The one or more connectors may be attached to the interior surface of each of the two flexible substrates within the channel. The one or more connectors may be attached to the exterior surface of each of the two flexible substrates. Alternatively, the device may comprise one or more connectors that extend across the width of the device that restrict the maximum extent to which at least one of the two flexible substrates may be bent. The device may comprise a rigid tertiary structure or a triangular lock fold that define the maximum extent the channel of the device may open.

The device may comprise a mouthpiece adjacent to or at the air outlet. Accordingly, during use the user may contact their mouth to the mouthpiece when the device is in the second configuration and then inhale through the mouthpiece. The mouthpiece may be the air outlet. The mouthpiece may be configured to provide support to the lips of a user during use.

The invention extends in a second aspect to a method of using a device according to the first aspect, the method comprising the steps:
(i) providing a device according to the first aspect;
(ii) applying pressure to the two opposed connected edges of the two flexible substrates of the device to thereby move the device from the first configuration, to the second configuration; and
(iii) inhaling adjacent to an opening of the device in the second configuration to thereby inhale an active agent from the membrane of the device through the channel and into the lungs.

When the device is in the second configuration, the user may contact their mouth to an opening of the channel. Therefore, the user may inhale through the device in step (iii). A seal may be formed between the device and the mouth of the user. Accordingly, when the user inhales, all or substantially all air that passes into the user's mouth has passed through the channel of the device and thereby carries active agent from the membrane of the device.

The user may apply pressure to the two opposed edges of the two flexible substrates by squeezing those edges toward each other.

In embodiments where the device comprises seals, step (ii) typically breaks said seals to thereby expose the membrane of the device.

In embodiments where the device is provided in packaging, the device is typically removed from said packaging prior to step (ii).

Once the user has inhaled through the device, the device may be discarded.

BRIEF DESCRIPTION OF THE FIGURES

Embodiments of the present invention will now be described, by way of non-limiting example, with reference to the accompanying drawings.

DETAILED DESCRIPTION

Figure 1:
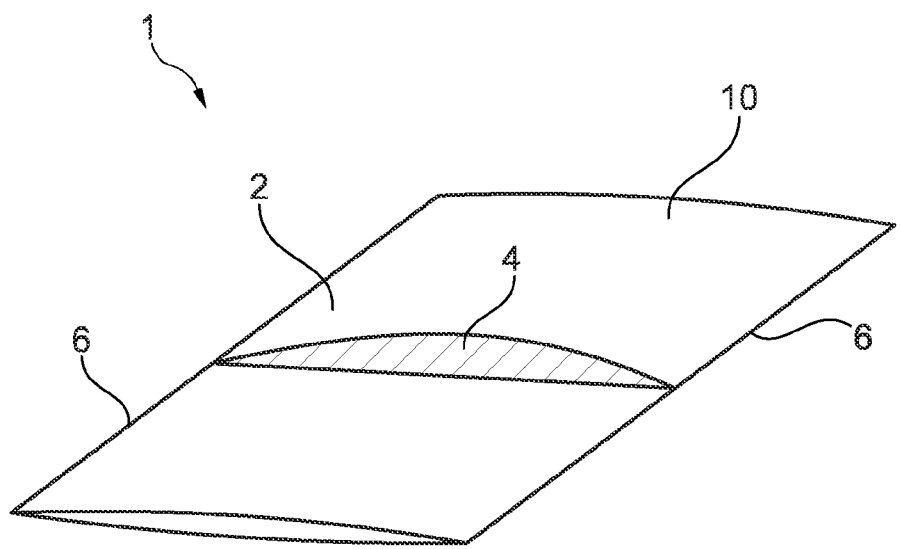
FIG. 1 shows a front perspective view of a device according to an embodiment of the invention in the closed or first configuration.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

With reference to FIGS. 1-7, an inhaler 1 comprises two rectangular card sheets 2 (acting as flexible substrates) and a mesh 4 (acting as a membrane). The two card sheets are connected at two opposing edges 6 such that the two card sheets occlude one another and have interior surfaces 8 and exterior surfaces 10. The mesh is connected to the interior surface of both card sheets. A particulate form of salbutamol 12 (corresponding to an active agent) is provided on the mesh.

Figure 2:
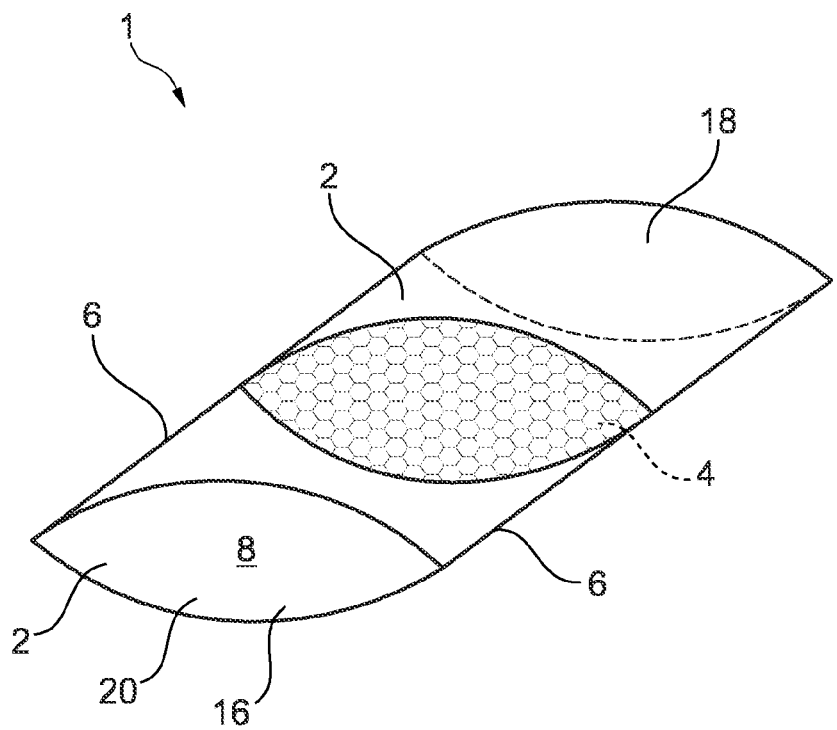
FIG. 2 shows a front perspective view of a device according to an embodiment of the invention in the open or second configuration.
Figure 3:
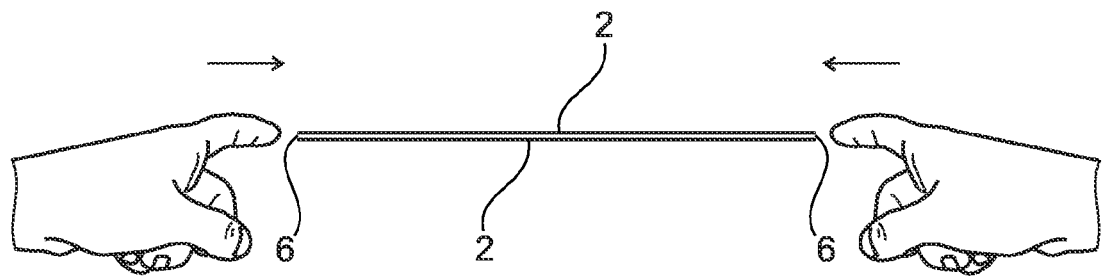
FIG. 3 is a front view of a device according to an embodiment of the invention in the first configuration showing a user applying pressure to sides of the device.
Figure 4:
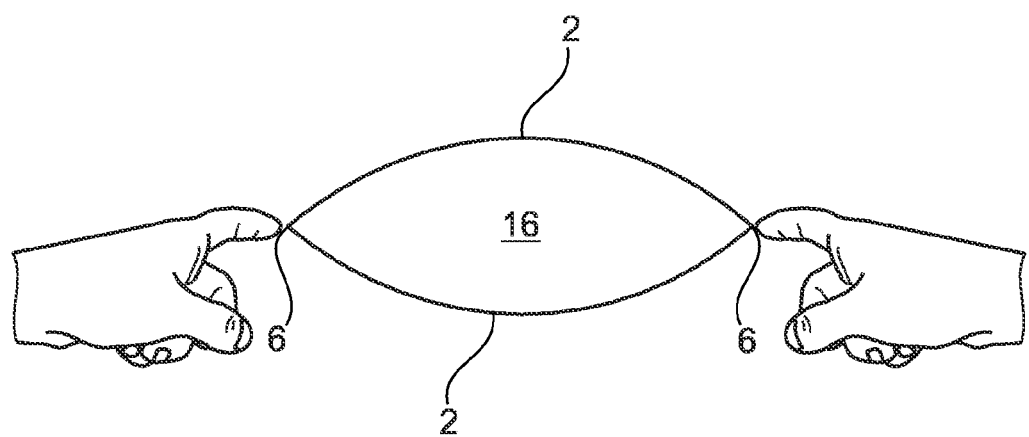
FIG. 4 is a front view of a device according to an embodiment of the invention showing the device in the open second configuration after pressure has been applied to the sides of the device.
Figure 5:
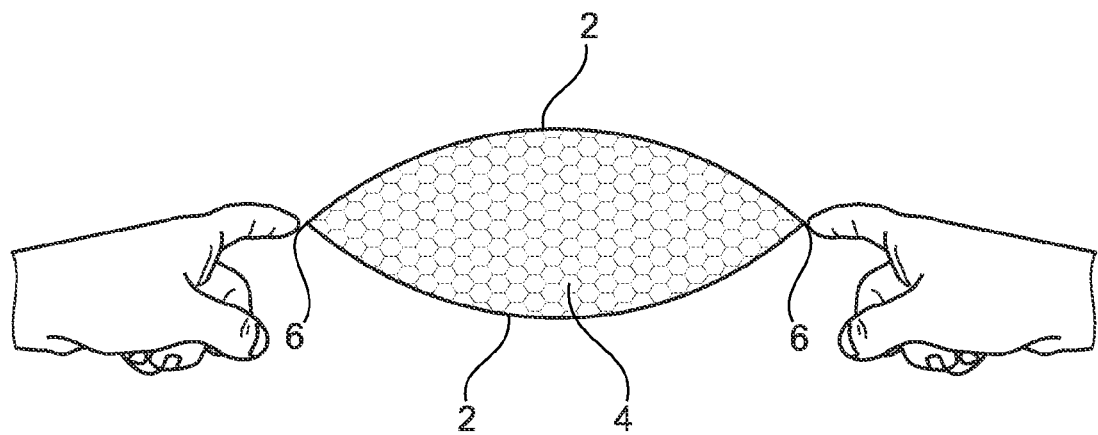
FIG. 5 shows a device according to an embodiment of the invention in the second open configuration.
Figure 6:
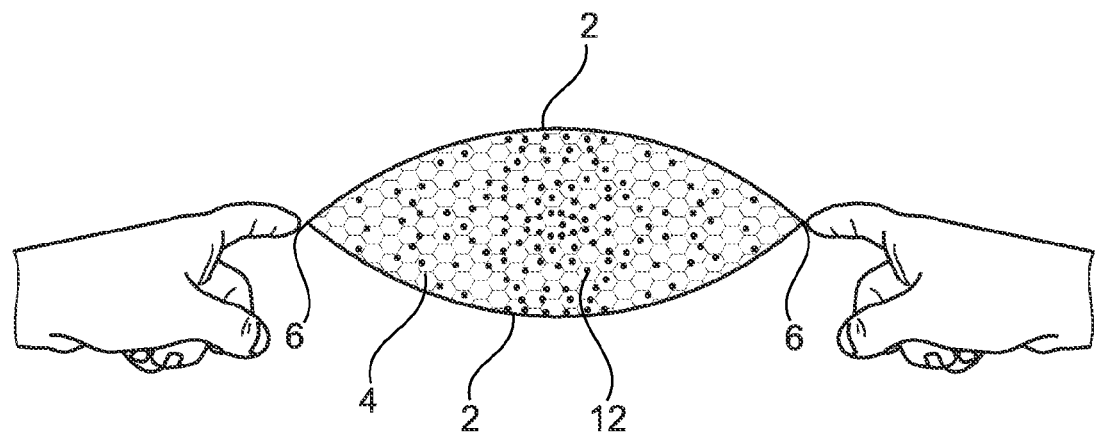
FIG. 6 shows a device according to an embodiment of the invention in the second open configuration.
Figure 7:
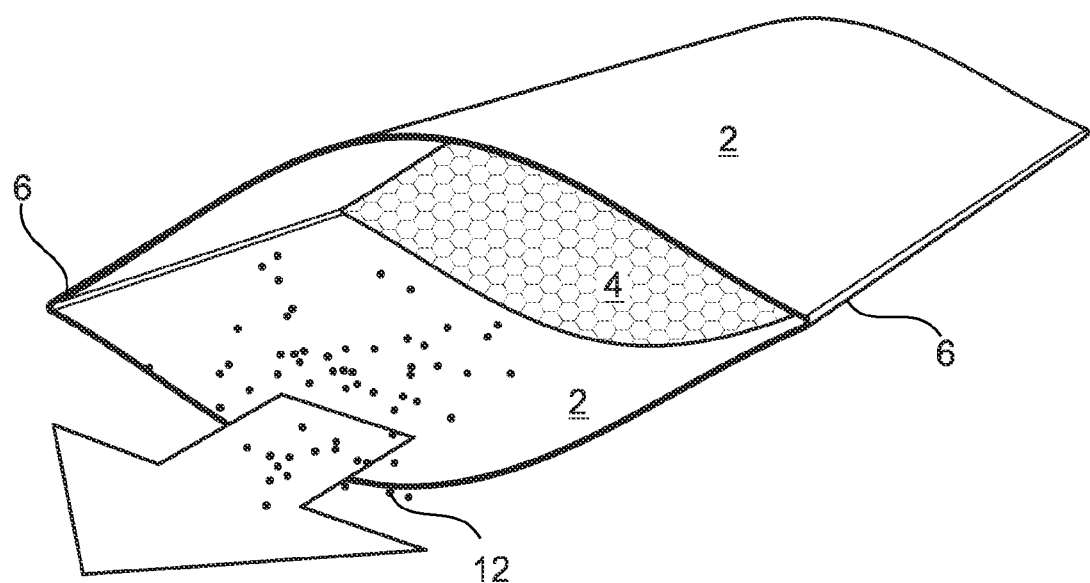
FIG. 7 shows a front perspective view of a device according to an embodiment of the invention.

The inhaler is configured to move between two configurations, a closed configuration as shown in FIG. 1 (corresponding to the first configuration) and an open configuration as shown in FIG. 2 (corresponding to the second configuration). In the closed configuration, the interior surfaces of the two card sheets are adjacent and the inhaler is flat. In the open configuration, a channel 16 is formed between the two card sheets and the mesh spans the channel. The channel has a first opening 18 and a second opening 20 and air flowing from the first opening to the second opening passes through the mesh to thereby lift the particles of salbutamol from the mesh.

The inhaler is retained before use in a sealed water proof envelope to ensure that the salbutamol on the mesh does not come into contact with water.

When the inhaler is to be used, the inhaler is removed from the water proof envelope. The user pinches the two sides of the inhaler that are connected together to move the inhaler from the closed configuration to the open configuration (see FIGS. 3 and 4). The inhaler is then brought into contact with the user's mouth to thereby form a seal around the second opening of the channel and the user inhales through the channel of the inhaler. Salbutamol particles are thereby lifted from the mesh and are drawn into the lungs of the user. The inhaler may then be discarded.

Figure 8:
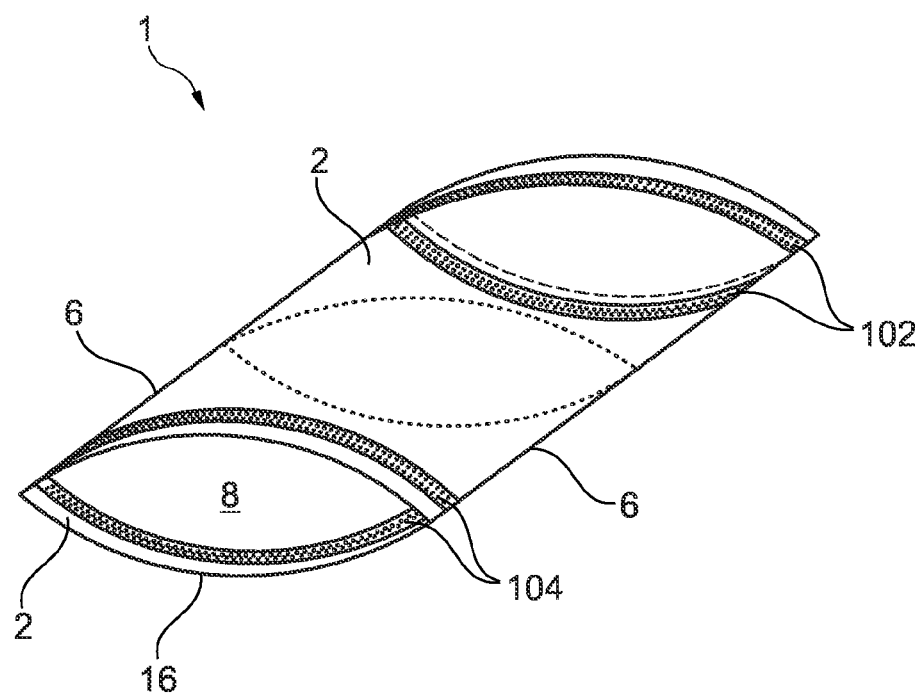
FIG. 8 shows a front perspective view of a device according to an embodiment of the invention.
Figure 9:
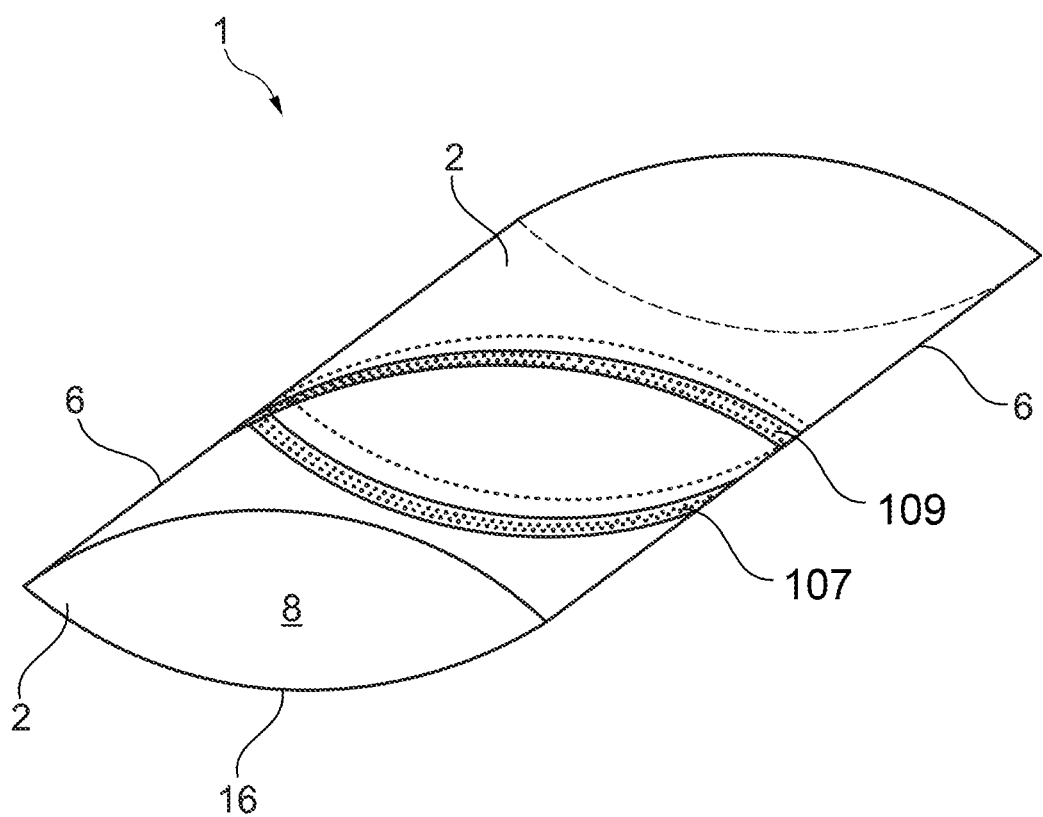
FIG. 9 shows a front perspective view of a device according to an embodiment of the invention.
Figure 13:
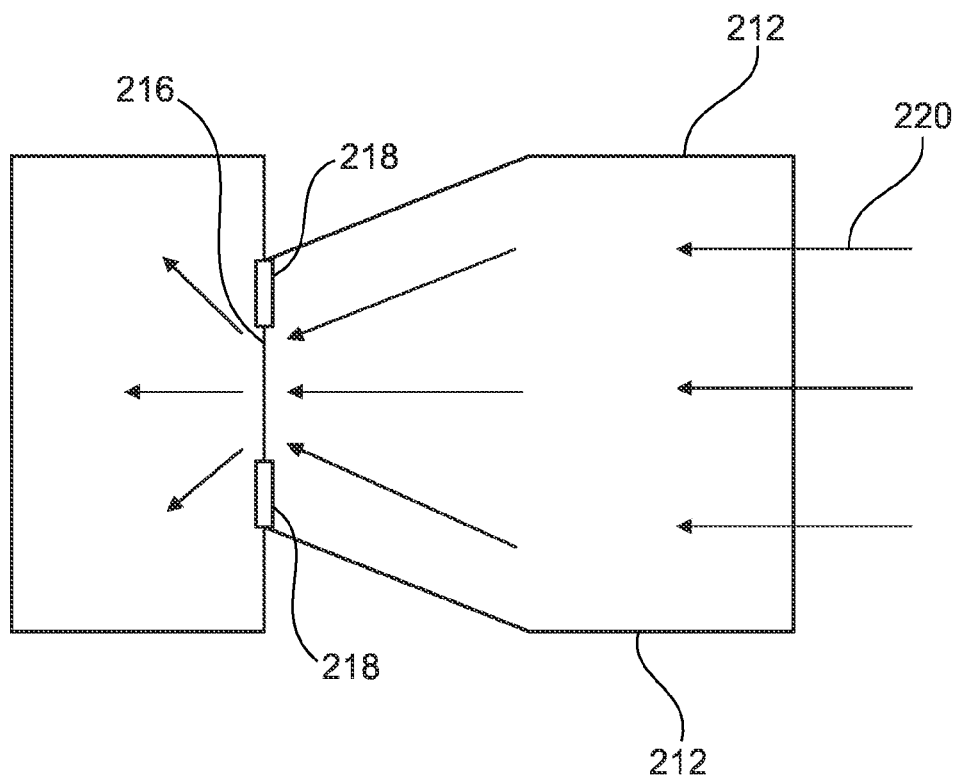
FIG. 13 is a schematic of the air flow through the device of FIG. 10 in the open second configuration.

In an alternative embodiment, with reference to FIG. 8, seals 102, 104 are provided between the interior surfaces of the two card sheets to thereby seal the mesh and the salbutamol retained thereon from moisture. Accordingly, it is not necessary to retain the inhaler of this embodiment in a sealed waterproof envelope. Instead, when the user needs to receive a dose of salbutamol, the seals are broken and the mesh exposed when the user squeezes the sides of the inhaler to move the inhaler from the closed configuration to the open configuration.

With reference to FIG. 16 in an alternative embodiment, a membrane 106 in a device is protected from moisture, light, and contamination by a foil lining 108 (acting as a metallic coating) on the interior of the channel. The foil lining is bounded at either side of the membrane by a seal 110, 112 such that the membrane is sealed within a foil envelope formed by the foil lining 108 of both interior surfaces of the channel. The foil envelope extends either side of the membrane (FIG. 16 A or 16 B). In one example, the foil envelope extends across a portion of the channel (FIG. 16A). In a second example, the foil envelope extends substantially along the entire length of the channel (FIG. 16B).

When the device is moved from the first configuration to the second configuration, the seals 110, 112 are broken and the membrane 106 is exposed for use.

In a further alternative embodiment, with reference to FIG. 9, the two card sheets comprise two reinforcing strips 107, 109 (corresponding to reinforcing elements). Each reinforcing strip is curved such that the device is biased towards the open configuration. Each reinforcing strip extends across one card sheet from one connected edge to the second connected edge. Accordingly, the reinforcing strips run across the channel when the inhaler is in the open configuration. When the inhaler is squeezed or compressed to move the inhaler from the closed configuration to an open configuration the user grips the device adjacent to the reinforcing strips and compresses the card sheets at the reinforcing strips.

Accordingly, the reinforcing strips assist the user to open the device by moving the device from the closed configuration to the open configuration.

In a yet further embodiment, the two card sheets comprise creases (not shown) acting as flexible regions that bias the device towards the open configuration. Accordingly, the device may more readily open when pressure is applied to the connected opposing edges by the user.

In another embodiment, the mesh comprises particles that comprise an inhalable form of insulin as the active agent.

With reference to FIGS. 10 to 13, in an alternative embodiment, a device 200 comprises two plastic coated card sheets 202, a membrane (not shown) mounted within a support 218 within a channel formed between the two sheets 202. The two sheets 202 comprise cuts 208 and creases 210, and are bonded to each other along two opposed edges 212, and are unconnected along two other opposed edges 214.

In a first configuration (shown in FIG. 10A) the two sheets 202 are flat and rectangular. In a second configuration (shown in FIG. 10B) the channel opens between the two sheets and the membrane 216 and support 218 unfold to span the channel. When the device is moved from the first configuration to the second configuration the user presses the sides adjacent to the cuts and creases as indicated by the arrows in FIG. 10A. As a result, the part of the flexible substrate between the cut and crease folds into the channel, thereby forming an aperture within the channel and changing the shape of the channel to form the second configuration as shown in FIG. 10B. The support 218 and membrane 216 span and occlude the aperture such that airflow 220 (represented by the arrows in FIG. 13) through the device is forced to pass through the membrane.

With reference to FIG. 13, air entering the device through the air inlet is moving at a given flow rate. As the cross-section of the channel narrows, the air is forced to accelerate to maintain the same flow rate. Accordingly, the air is forced to accelerate through the aperture and membrane, thereby applying a higher force on the active agent on the membrane to lift that active agent into the airflow from the membrane.

Figure 10A:
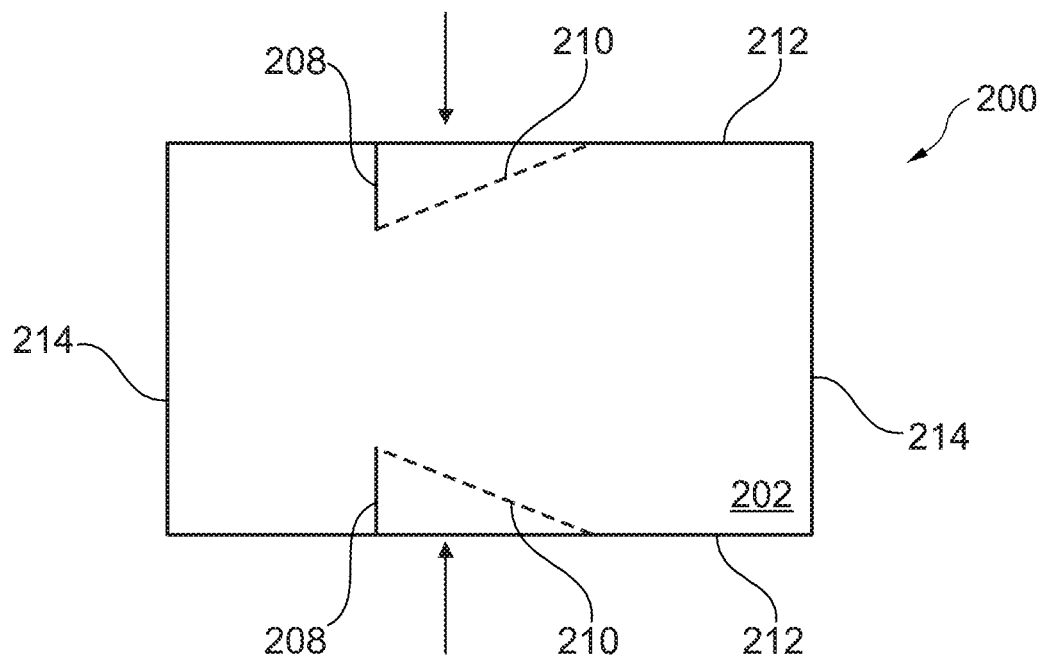
FIG. 10 is a plan view of a device according to an embodiment in (A) the closed first configuration and (B) in the open second configuration.
Figure 10B:
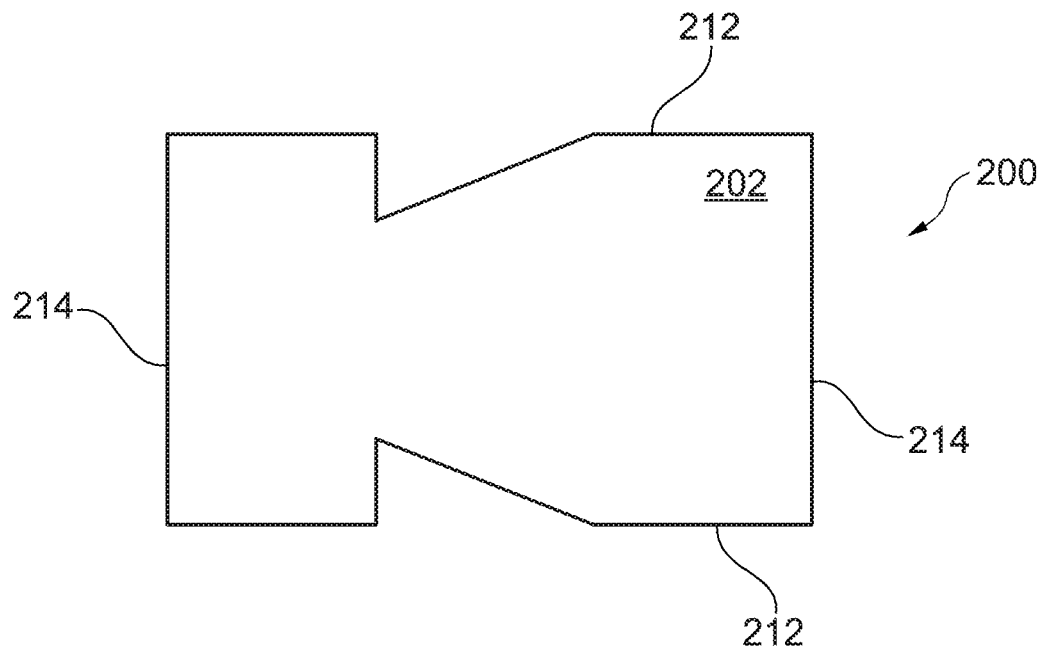
Figure 11:
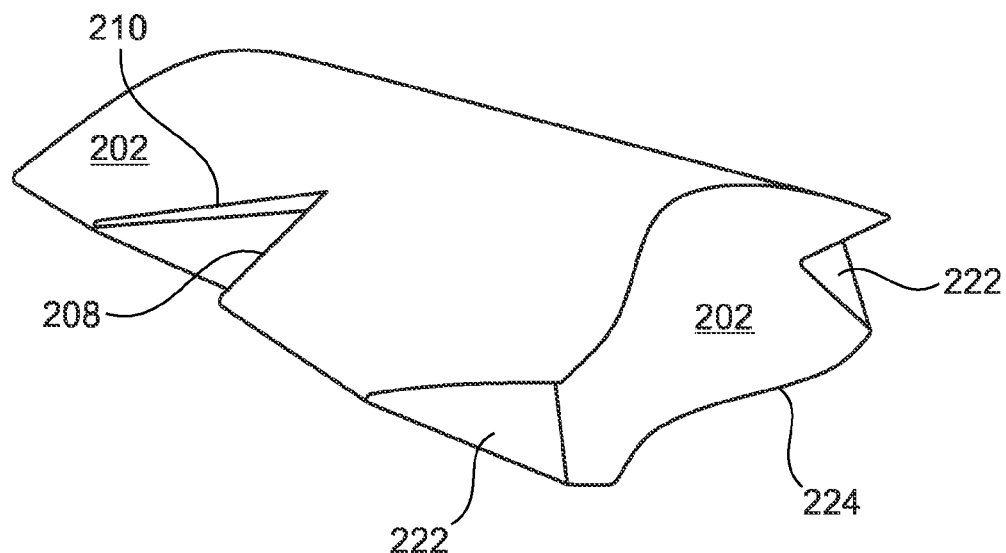
FIG. 11 is a front perspective view of an embodiment of the invention.
Figure 12:
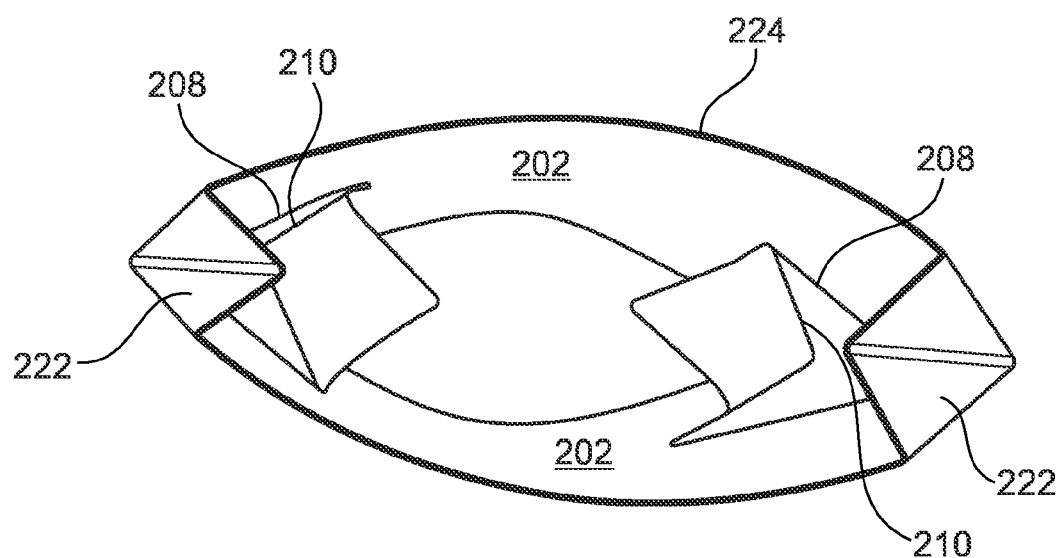
FIG. 12 is a front view of the device of FIG. 11.

A variation of the device shown in FIG. 10 is shown in 3D in FIGS. 11 and 12. The device further comprises supports 222 at the air outlet that 224. The supports 222 brace the air outlet to resist excessive force being applied to the device by the mouth of the user. The front view of the device shown in FIG. 12 does not show the membrane of the device to allow the channel to be seen in full.

Figure 14A:
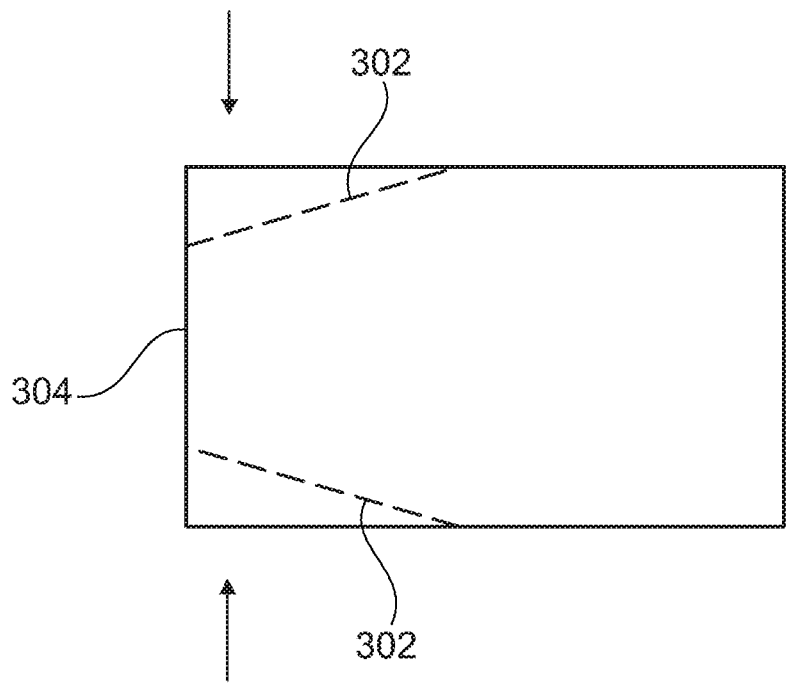
FIG. 14 is plan views of a device according to an embodiment of the invention in (A) the closed first configuration and (B) in the open second configuration.
Figure 14B:
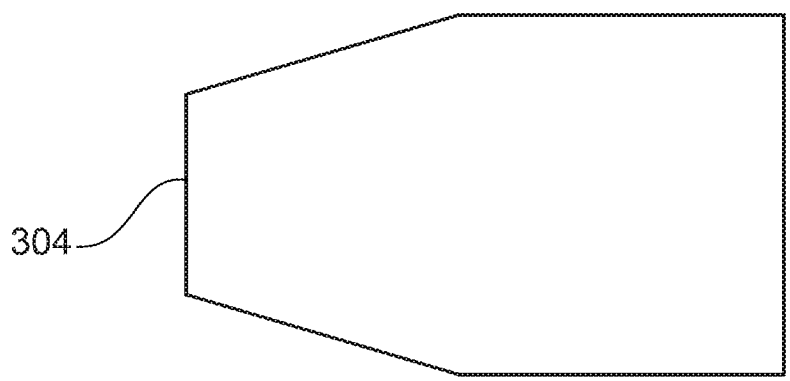
Figure 15:
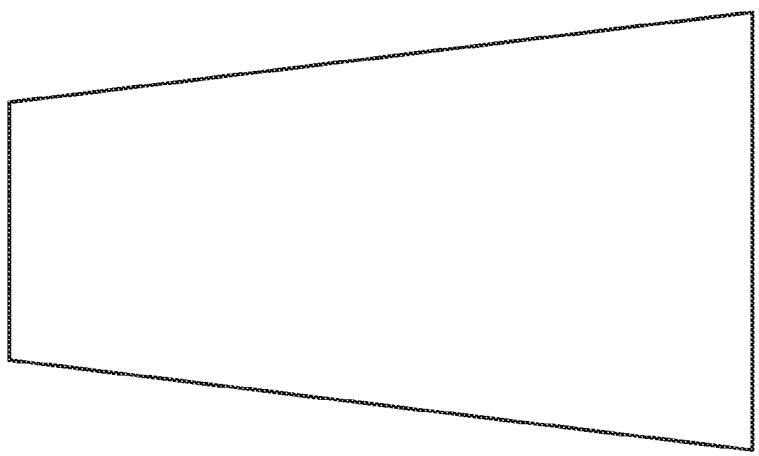
FIG. 15 is a plan view of a device according to an embodiment.
Figure 16A:
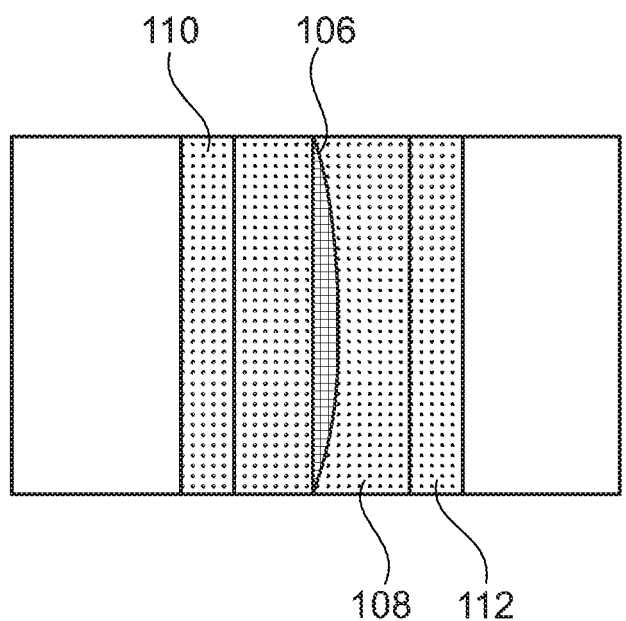
FIGS. 16 (A) and (B) shows plan views of two devices showing different configurations of foil envelopes protecting the membrane in the first configuration.
Figure 16B:
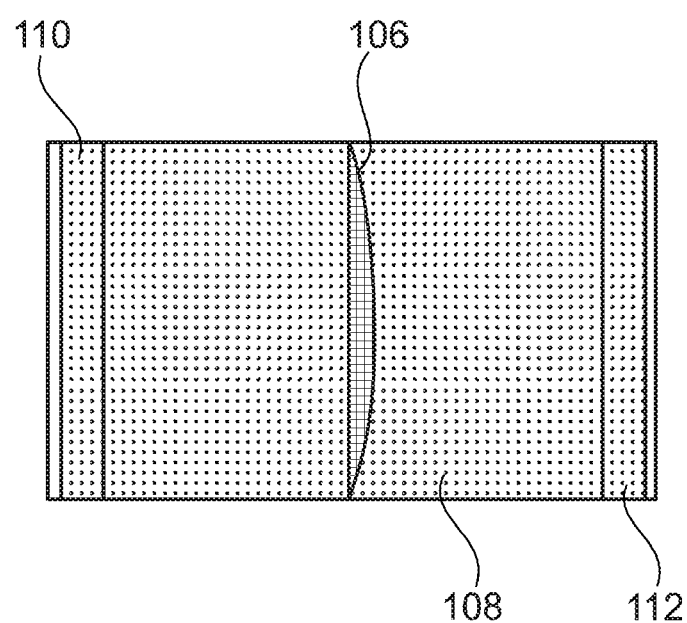

A similar effect may be achieved by devices with channels that narrow to an aperture such as those shown in FIGS. 14 and 15. For example, FIG. 14A shows a device where the flexible sheets comprise creases 302. When the device is moved from the first configuration to the second configuration, the device is squeezed by the user as indicated by the arrows in FIG. 14A such that the width of the air outlet 304 is reduced.

Figure 17A:
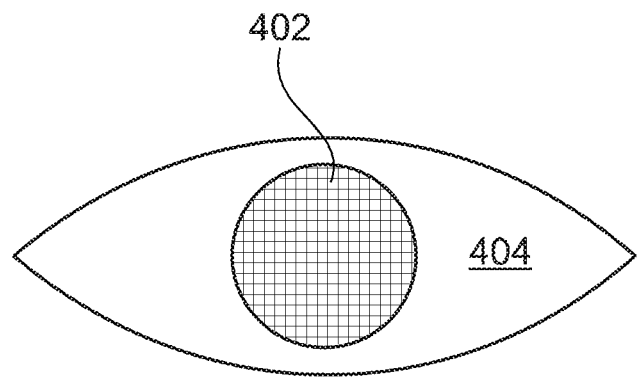
FIG. 17 (A) is a front view of a device according to an embodiment where the membrane is mounted in a support, and (B) shows an exploded view of the membrane and support.
Figure 17B:
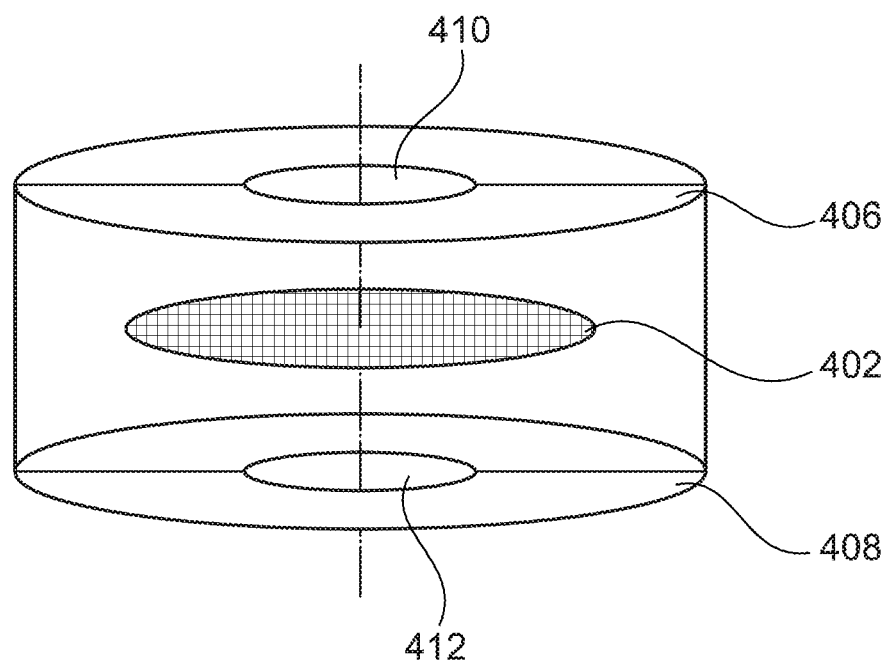
Figure 18:
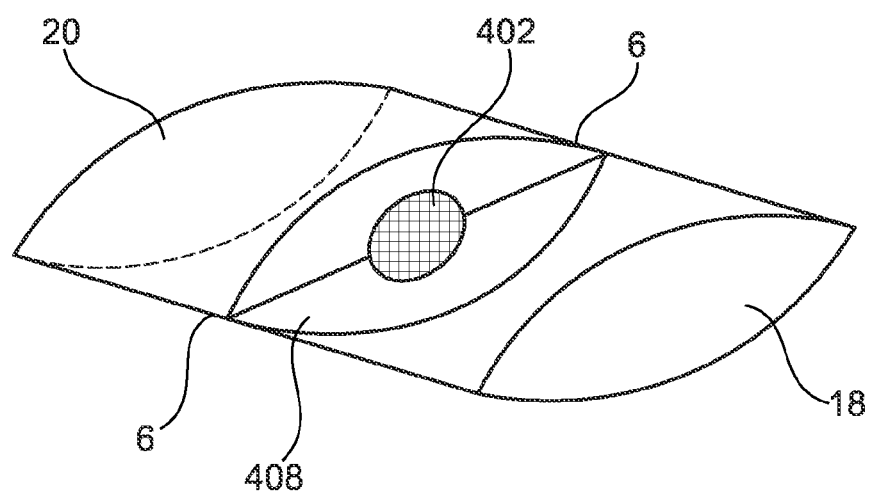
FIG. 18 is a front perspective view of a device according to an embodiment comprising a membrane mounted in a support.

A membrane 402 mounted in a support 404 is shown in FIG. 17A. The membrane 402 is sandwiched between two support layers 406, 408 and occludes an aperture 410, 412 in the two support layers 406, 408. The two support layers 406, 408 are typically bonded together with a bonding agent such as glue or similar.

It will be appreciated by the person skilled in the art that the above embodiments are examples and that the features of each disclosed embodiment may be combined with the features of other embodiments. Further variations and modifications are herein contemplated and included in the present invention.

The invention claimed is:

1. A device comprising two flexible substrates and a membrane located between the two flexible substrates, the two flexible substrates being connected at two opposing edges and unconnected at a first end having a first opening with two further opposing edges and a second end having a second opening with two further opposing edges, wherein the device is configured to move between a first configuration where the two flexible substrates are substantially flat and the opposing edges defining the first opening are in contact with one another and the opposing edges defining the second opening are in contact with one other, and a second configuration where the two flexible substrates are flexed and the opposing edges defining the first opening are not in contact with one other and the opposing edges defining the second opening are not in contact with one other such that a channel is formed between the two flexible substrates, wherein the membrane is configured to span the channel between the two flexible substrates when the device is in the second configuration, such that an active agent provided on the membrane may be inhaled by a user when the device is in the second configuration, and wherein each of the two flexible substrates comprises a reinforcing element which are parallel to each other in the first configuration, and wherein each reinforcing element biases the device toward the second configuration.

2. The device according to claim 1, wherein the two flexible substrates are rectangular, square or oblong.

3. The device according to claim 1, wherein the two flexible substrates are biodegradable.

4. The device according to claim 1, wherein at least a portion of one or both of the two flexible substrates comprises a metallic coating.

5. The device according to claim 1, wherein the cross-section of the channel is reduced in a portion of the channel.

6. The device according to claim 1 comprising a seal at either side of the membrane.

7. The device according to claim 6, wherein the seals are adjacent to the openings of the channel.

8. The device according to claim 6, wherein the seals are adjacent to the membrane.

9. The device according to claim 1, wherein each reinforcing element is adjacent to one or both openings of the channel.

10. The device according to claim 1, wherein each reinforcing element is a strip of material that is stiffer than the flexible substrates.

11. The device according to claim 1, wherein the membrane is a mesh.

12. The device according to claim 1, wherein the membrane is air permeable.

13. The device according to claim 1, wherein the membrane is mounted to both flexible substrates.

14. The device according to claim 1, wherein the membrane is flexible and is folded or collapsed when the device is in the first configuration.

15. The device according to claim 1, wherein the active agent is present on the membrane.

16. The device according to claim 15, wherein the active agent is in particulate form.

17. The device according to claim 1, wherein the active agent is an inhalable active agent selected from the group: tramadol, gabapentin, Vicodin (registered trademark), ibuprofen, acetaminophen, hydrocodone, naproxen, methadone, codeine, hydroxyzine, paracetamol, aspirin, insulin, canagliflozin, alogliptin benzoate, dapagliflozin, empagliflozin, ranibizumab, duglaglutide, pioglitazone hydrochloride, glimepiride, oxytocin, and sildenafil.

18. A method of using a device according to claim 1, the method comprising the steps:
 (i) providing a device according to claim 1;
 (ii) applying pressure to the two opposed connected edges of the two flexible substrates of the device to thereby move the device from the first, closed configuration, to the second, open configuration; and
 (iii) inhaling adjacent to an opening of the device in the second configuration to thereby inhale the active agent from the membrane of the device through the channel and into the lungs.

19. The method according to claim 18, wherein the user contacts their lips to an opening of the device in the second configuration to thereby form a seal around that opening before inhaling the active agent.

20. The device according to claim 1, wherein each reinforcing element are in contact with one another in the first configuration.

* * * * *